(12) United States Patent
Ekberg et al.

(10) Patent No.: US 7,510,629 B2
(45) Date of Patent: Mar. 31, 2009

(54) METHOD AND DEVICE FOR ANALYSING SURFACE STRUCTURE IN PAPER OR BOARD

(75) Inventors: Magnus Ekberg, Avesta (SE); Per-Olof Ersson, Falun (SE); Olle Henningsson, Falun (SE); Karin Oldberg, Avesta (SE); Tomas Oldberg, Avesta (SE); Karl-Heinz Rigerl, Falun (SE); Bosse Wigge, Gustafs (SE)

(73) Assignee: Stora Enso AB, Karlstad (SE)

( * ) Notice: Subject to any disclaimer, the term of this patent is extended or adjusted under 35 U.S.C. 154(b) by 375 days.

(21) Appl. No.: 10/563,780

(22) PCT Filed: Jun. 28, 2004

(86) PCT No.: PCT/SE2004/001052

§ 371 (c)(1),
(2), (4) Date: May 30, 2006

(87) PCT Pub. No.: WO2005/004042

PCT Pub. Date: Jan. 13, 2005

(65) Prior Publication Data

US 2006/0272788 A1 Dec. 7, 2006

(30) Foreign Application Priority Data

Jul. 8, 2003 (SE) .................... 0302011

(51) Int. Cl.
*D21F 11/00* (2006.01)
(52) U.S. Cl. ............... 162/198; 162/263; 382/112; 382/128; 382/228; 382/218; 356/445; 356/124.5
(58) Field of Classification Search ............... 162/198, 162/263; 382/112, 128, 228, 195, 218, 149, 382/141, 308; 356/445
See application file for complete search history.

(56) References Cited

U.S. PATENT DOCUMENTS 5,155,558 A 10/1992 Tannenbaum et al.
6,266,437 B1 * 7/2001 Eichel et al. ............... 382/149

2002/0054694 A1 5/2002 Vachtsevanos et al.

FOREIGN PATENT DOCUMENTS

| EP | 0366235 | 5/1990 |
|---|---|---|
| SE | 516 999 | 4/2002 |
| WO | WO 03 039156 | 5/2003 |

OTHER PUBLICATIONS

International Search Report from PCT/SE2004/001052.

* cited by examiner

*Primary Examiner*—Mark Halpern
(74) *Attorney, Agent, or Firm*—Greer, Burns & Crain, Ltd.

(57) ABSTRACT

A method for analyzing in real-time in a paper machine or board machine the surface structure of a web (1) of paper or board which method comprises the direction of an imaging system towards a pre-determined area (3) of the web (1), the arrangement of an illumination system to illuminate the region from a pre-determined direction with obliquely incident light, and the arrangement of an image analysis system in association with the imaging system. Furthermore, the method comprises, according to the invention, an image capture step (7) in which the imaging system is caused to take several digital images of the web under the said oblique incident illumination and during a pre-determined period, which images form an image sequence that images a series of surface sections (4, 4', 4") along a band (8) in the web (1), and an evaluation step (9) that is carried out by the image analysis system and which comprises an image analysis step (11), which in turn comprises a first analysis operation (16) in which the variance of the pixel values in each pixel row in each image in the image sequence is determined within a pre-determined wavelength band, and a second analysis operation (17) in which the mean value of the variances of all pixel rows of all images in the image sequence is calculated. The invention also concerns a device for the execution of the method.

9 Claims, 3 Drawing Sheets

METHOD AND DEVICE FOR ANALYSING SURFACE STRUCTURE IN PAPER OR BOARD

This application is a 371 of PCT/SE04/01052 filed on 28 Jun. 2004.

FIELD OF THE INVENTION

The present invention concerns a method for real-time analysis of the surface structure of a web in a paper or paperboard machine.

The present invention also concerns a device for real-time analysis of the surface structure of a web in a paper or paperboard machine.

The method and the device according to the invention are particularly suitable for determining the quantity and the severity of defects in the form of shrinkage creases or other types of crease in the web.

BACKGROUND OF THE INVENTION

During the manufacture of a web of paper or board in a paper machine or a board machine, and in particular during the production of board from chemo-thermo mechanical pulp (CTMP), it is not unusual that shrinkage creases, which extend along the longitudinal direction of the web, form. The shrinkage creases constitute an undesirable defect of the web that should be reduced as much as is possible by changing the settings of the board machine.

One method that is used to assess the appearance of the web and the occurrence of shrinkage creases is to allow an operator to inspect the web visually, for example during exchange of machine roll, and to estimate the extent of the shrinkage creases. The operator can, for example, estimate the extent on associated with such a procedure. Firstly, the procedure is subjective, i.e. there is a risk that different operators will estimate the extent of the same shrinkage creases differently. Secondly, the area of inspection is limited to that part of the web that is visible at the machine roll, i.e. the part of the web that forms the covering surface of the machine roll. Thirdly, it is only possible to discover relatively major changes in a visual inspection. In other words, the resolution of a visual inspection is relatively low.

One way of objectively measuring the surface structure of a web of paper is described in the patent SE 516999. According to the method described, two images of the web are taken in the transverse direction of the web at a pre-determined position. The web is illuminated for the two images by light obliquely incident from two different directions, i.e. the web is illuminated with light that is incident from a first direction during the taking of the first image, and it is illuminated with light incident from a second direction during the taking of the second image. The images are subsequently Fourier-transformed and the spectra obtained are combined to give an approximation of the correct spectrum of the web. It has, however, become apparent that this method of measuring the surface structure of the web is less suitable when shrinkage creases are present. In particular, the step of taking two images with illumination from two different directions is inconveniently complex.

SUMMARY OF THE INVENTION

The aim of the present invention is to achieve a method and a device that are particularly suitable for determining in real time the quantity and the severity of shrinkage creases.

The method according to the invention is analysing in real-time in a paper machine or board machine the surface structure of a web produced in a paper machine or a board machine, which method comprises:

that an imaging system is arranged above or below the web and is directed towards a pre-determined area of the web, that an illumination system is arranged above or below the web in order to illuminate the area from a pre-determined direction with obliquely incident light, and that an image analysis system is arranged in association with the imaging system, wherein the method further comprises:

an image capture step in which the imaging system is caused to take several digital images of the web under the said oblique incident illumination and during a pre-determined period, when the web passes in front of the imaging system, which images form an image sequence that images a series of surface sections along a band in the web, and an evaluation step that is carried out by the image analysis system and which comprises an image analysis step, that comprises a first analysis operation in which the variance of the pixel values in each pixel row in each image in the image sequence is determined within a pre-determined wavelength band, and a second analysis operation in which the mean value of the variances of all pixel rows of all images in the image sequence is calculated.

The device according to the invention is for the real-time analysis in a paper machine or a board machine of the surface structure of a web of paper or board produced in a paper machine or a board machine, which device comprises:

an imaging system that is arranged above or below the web and is directed towards a pre-determined area of the web, an illumination system that is arranged above or below the web in order to illuminate from a pre-determined direction the area with obliquely incident light, and an image analysis system that is arranged to be in communication with the imaging system, wherein the imaging system is arranged to take under the illumination and during a pre-determined period several digital images of the web when the web passes in front of the imaging system, which images form a series of surface sections along a band in the web, and the image analysis system is arranged to calculate the variance in the pixel values in each pixel row in each image in the image sequence, and to calculate the mean value of the variances of all pixel rows of all images in the image sequence.

The invention will be described in more detail with reference to the figures.

DETAILED DESCRIPTION OF A PREFERRED EMBODIMENT

Figure 1:
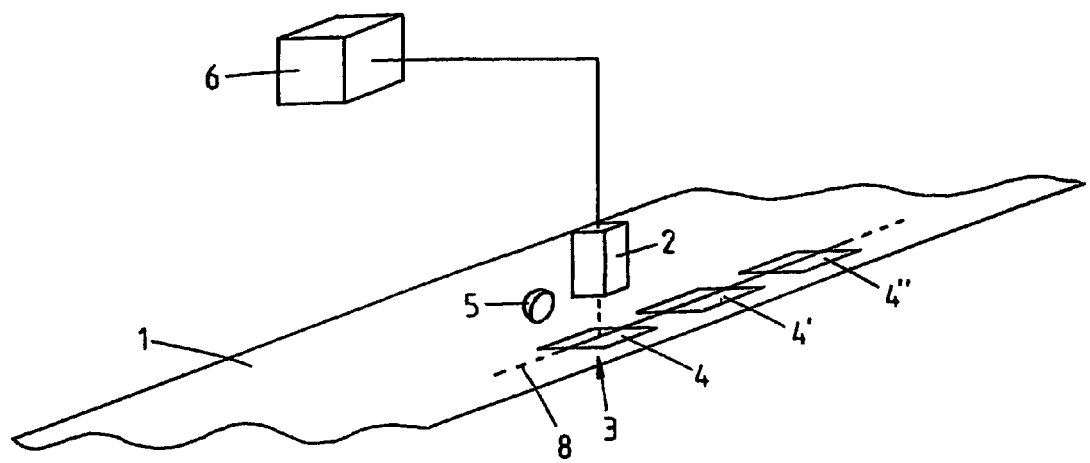
FIG. 1 shows schematically and in principle a device according to one preferred embodiment of the invention.

FIG. 1 shows a device for determining in real-time the quantity and the severity of shrinkage creases that form in a web 1 of board when the web 1 is manufactured in a board machine (not shown in the figure). The device comprises an imaging system, which comprises a camera 2 in the form of a digital CCD camera of the type known as "progressive scan". The camera 2 is arranged above the web 1 and is directed towards a pre-determined area 3 of the web 1, in which area 3 it is desired to analyse the surface structure of the web 1. In the present case, the area 3 is located at one edge section of the web 1. The imaging angle of the camera 2 and the distance between the camera 2 and the web 1 are chosen such that it is possible for the camera 2 to image in the said area 3 a surface section 4 of a pre-determined size of the web 1 when the web 1 passes in front of the camera 2. The device further comprises an illumination system, which comprises a lamp 5 arranged at a pre-determined position above the web in order to illuminate the area 3 with obliquely incident light. The position of the lamp 5 in the present case is at the same height as the camera 2 in the longitudinal direction of the web 1, and the axis of illumination of the lamp 5 forms an angle with the web 1 that lies in the interval 1-15°. The lamp 5 can, however, be placed at another position that provides illumination of the area 3 with obliquely incident light. It is preferable that the lamp 5 comprises a xenon incandescent lamp that provides the required light intensity in a suitable wavelength interval. Other light sources can, however, be used. The device also comprises an image processing system, which comprises a computer 6.

Figure 2:
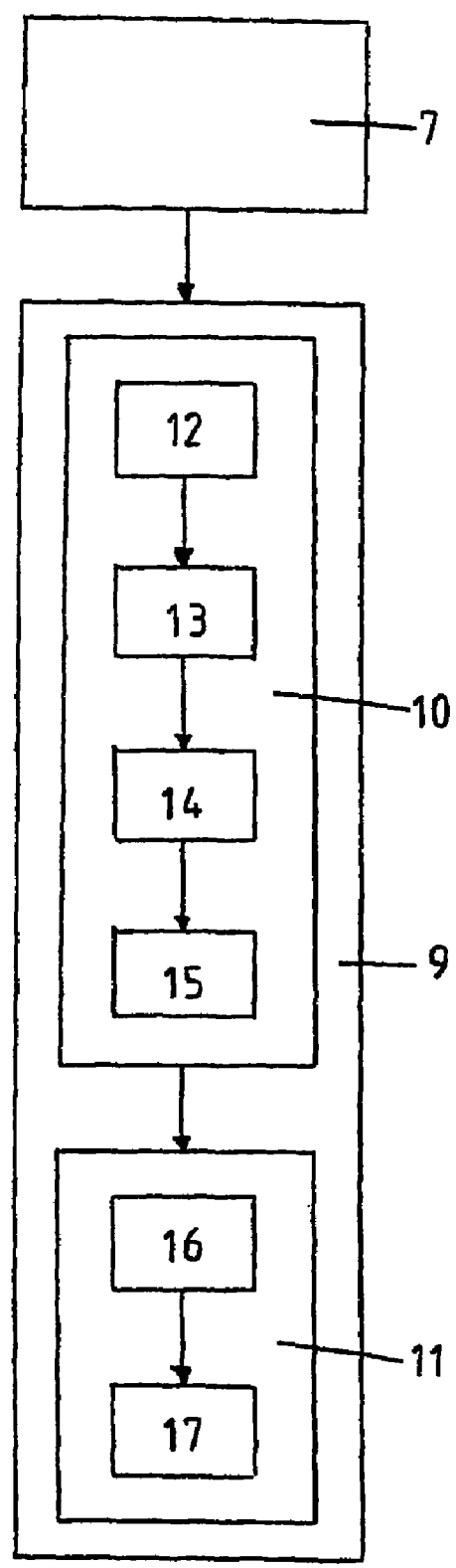
FIG. 2 shows a flow chart that illustrates one preferred sequence of steps in order to determine the quantity and the severity of shrinkage creases according to the invention.
Figure 3:
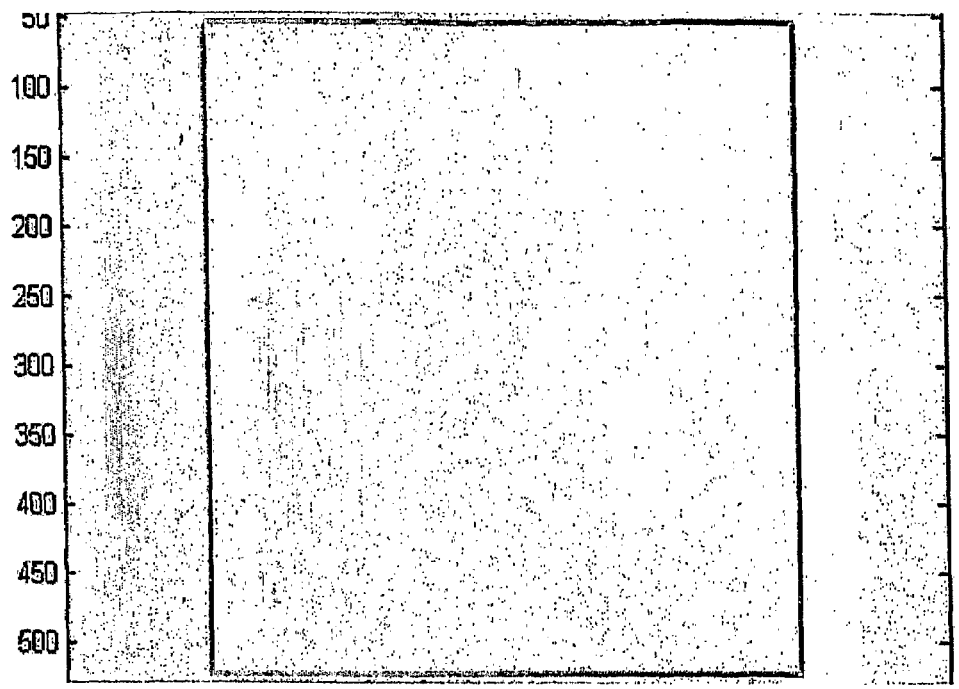
FIG. 3 shows an image of a surface section of a web of board that demonstrates shrinkage creases.
Figure 4:
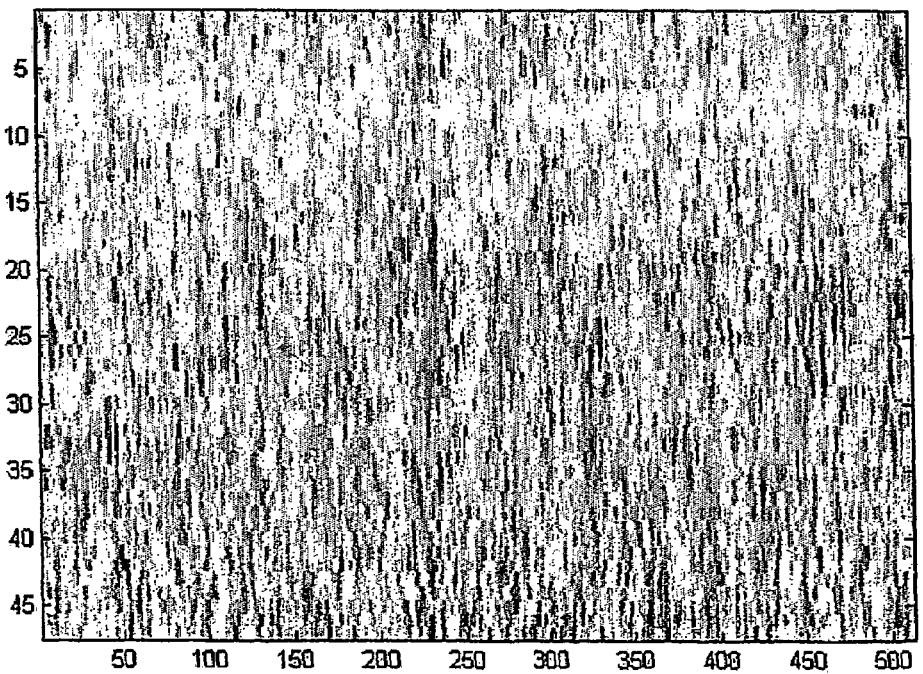
FIG. 4 shows the image according to FIG. 3 following an image processing step according to the invention.

A preferred sequence of steps of determining the quantity and the severity of shrinkage creases using the device described above will be described below with reference to FIGS. 2-4.

The initial step is an image capture step 7 in which the camera 2 is caused to capture a pre-determined number of images of the web 1 in the light from the lamp 5 as the web 1 passes in front of the camera 2. The images thus form an image sequence that represents a series of surface sections 4, 4', 4", ... along a band 8 in the web 1. A suitable sequence of images may, for example, consist of 50 images taken during a duration of 2 seconds. FIG. 3 shows an illuminated surface section from such a sequence, which surface section extends vertically in the figure approximately 0.200 meter along the longitudinal direction of the web and horizontally in the figure approximately 0.267 meter in the transverse direction of the web 1. The camera 2 has in the present case imaged surface sections such as a digital image with a height of 580 pixel lines and a width of 770 pixel columns. Shrinkage creases appear in FIG. 3 as dark bands that have an extent in the longitudinal direction of the surface section, i.e. vertically in FIG. 3.

The images are transferred to the computer 6 after the image capture step 7, whereby an evaluation step 9 commences. The evaluation step 9 comprises a preparative image processing step 10 and a subsequent image analysis step 11.

The computer 6 carries out a sequence of image operations on each of the images during the image processing step 10. The aim of this step is to reduce contributions from disturbing sources of error, such as, for example, irregular and varying illumination, and to prepare the images for the subsequent image analysis step 11. A first image operation 12 comprises the division of each pixel value in each image with the mean pixel value of the image, after which each pixel value is multiplied by a pre-determined factor, for example 100. A second image operation 13 comprises the cropping of the edges of the image such that the image obtains pre-determined dimensions. The rectangle in FIG. 3 indicates such a cropping operation, in which the cropped image has a height of 470 pixel rows and a width of 512 pixel columns. A third image operation 14 comprises the division of the image into groups along the longitudinal direction of the web 1 with a pre-determined number of consecutive pixel rows in each group, after which new pixel rows are formed through the calculation of the mean value of the pixel values in each pixel column in each group and the assignment of this mean value to the pixels in the new pixel row. A fourth image operation 15 comprises the high-pass filtration of the image in the transverse direction. It is preferable that the high-pass signal is calculated through the subtraction from the original image of a low-pass signal obtained, for example, by causing an FIR Blackman filter to operate on the image. FIG. 4 shows the image according to FIG. 3 after the image operations specified above, where there are formed 47 groups with 10 pixel rows in each group during the third image operation, after which 47 new pixel rows are formed through the calculation of the mean value of the pixel values in each pixel column in each group and its assignment to the pixels in the new pixel row. FIG. 4 makes it apparent that the visible uneven illumination seen in FIG. 3 has been reduced through the image operations. Thus, a series of images is obtained from the image processing step 10, which in the present case has a height of 47 pixel rows and a width of 512 pixel columns, in which contributions from disturbing sources of error have been reduced.

The image analysis step 11 commences after the image processing step 10. The image analysis step 11 comprises a first analysis operation 16, in which the variance of the pixel values in each pixel row in each image is calculated within a pre-determined spatial wavelength band. This analysis operation 16 preferably takes place through the Fourier transformation of each pixel row with the aid of an FFT algorithm, after which the variance within the pre-determined band of wavelengths is calculated. Thus, this Fourier transform is one-dimensional. It has become apparent by comparing the visual ranking results using various wavelength bands that a wavelength band comprising the wavelengths 0.7-4 mm correlates well with the irregularities that shrinkage creases cause in board. Other wavelength bands may be relevant for paper. For example, a wavelength band comprising 3-15 mm has proved to be suitable for irregularities that folds in fine paper cause. The image analysis step 11 further comprises a second analysis operation 17, in which the mean values of the variance of all pixel rows for all images in the series are calculated and displayed on a monitor or stored for future evaluation. This mean value of the variance constitutes a measure of the quantity and the severity of shrinkage creases in the web 1, and an operator can rapidly and easily see trends in shrinkage creasing by comparing the mean value of the variance with results from previously evaluated image sequences, and take suitable measures.

Shrinkage creases can occur over the complete width of the web, but they occur principally at the edge sections of the web. It is therefore preferred that a device according to the invention is directed towards one edge section of the web, as is shown in FIG. 1. It will, however, be realised that the arrangement can comprise several imaging and illumination systems that are directed towards different parts of the web. For example, one imaging system and the associated illumination system can be directed towards the second edge section of the web, and an imaging system and its associated illumination system can be directed towards the central section of the web. It is thus possible, by using an arrangement comprising several pairs of imaging systems and illumination systems, to determine in real-time the quantity and the severity of shrinkage creases across the complete width of the web. Alternatively, one pair of an imaging system and an illumination system can be arranged such that it is possible to traverse across the web, and in this way the same imaging system can be used to image different parts of the web or the complete web. The imaging systems and the illumination systems can be arranged above the web, below the web, or both above and below the web.

One preferred sequence of steps for determining the quantity and the severity of shrinkage creases in a web has been described above. It will, however, be realised that the imaging and analysis operations described can be varied within the framework of the invention. Certain operations can be omitted or can be modified and other operations can be added without the deviating from the principle of the invention. It will also be realised that those parts that are included in a device according to the invention can be varied without deviating from the principle of the invention. For example, a linear recording CCD camera can be used instead of the said camera of "progressive scan" type. In such a case, the said images would be constituted by several lines, which form a sequence that images a surface section along a band in the web.

The invention claimed is:

1. A method for analysing in real-time in a paper machine or board machine the surface structure of a web produced in a paper machine or a board machine, which method comprises:
    that an imaging system is arranged above or below the web and is directed towards a pre-determined area of the web,
    that an illumination system is arranged above or below the web in order to illuminate the area from a pre-determined direction with obliquely incident light, and
    that an image analysis system is arranged in association with the imaging system,
    wherein the method further comprises:
    an image capture step in which the imaging system is caused to take several digital images of the web under the said oblique incident illumination and during a pre-determined period, when the web passes in front of the imaging system, which images form an image sequence that images a series of surface sections along a band in the web, and
    an evaluation step that is carried out by the image analysis system and which comprises an image analysis step, that comprises a first analysis operation in which the variance of the pixel values in each pixel row in each image in the image sequence is determined within a pre-determined wavelength band, and a second analysis operation in which the mean value of the variances of all pixel rows of all images in the image sequence is calculated.

2. The method according to claim 1, wherein the first analysis operation comprises the Fourier transformation of each pixel row with the aid of an FFT algorithm, after which the variance in the said wavelength band is calculated.

3. The method according to claim 2, wherein the web is board and the wavelength band comprises the wavelengths 0.7-4 mm.

4. The method according to claim 2, wherein the web is paper and the wavelength band comprises the wavelengths 3-15 mm.

5. The method according to claim 1, wherein the evaluation step also comprises an image processing step, which precedes the image analysis step, in order to reduce contributions from disturbing sources of error.

6. The method according to claim 5, wherein the image processing step comprises:
    a first image operation, in which each pixel value in each image in the image sequence is divided by the mean pixel value of the image and multiplied by a pre-determined factor,
    a second image operation, in which the edges of the image are cropped such that the image obtains pre-determined dimensions,
    a third image operation, in which the image is divided along the longitudinal direction of the web into groups with a pre-determined number of consecutive pixel rows in each group, after which new pixel rows are formed by the calculation of the mean value of the pixel values in each pixel column in each group and its assignment to the pixels in the new pixel row, and
    a fourth image operation, in which the image is high-pass filtered in the transverse direction of the web.

7. The method according to claim 6, wherein the said high-pass filtration occurs through the calculation of a low-pass signal and its subtraction from the image.

8. The method according to claim 7, wherein the said low-pass signal is obtained through an FIR Blackman filter being caused to operate on the image.

9. A device for the real-time analysis in a paper machine or a board machine of the surface structure of a web of paper or board produced in a paper machine or a board machine, which device comprises:
    an imaging system that is arranged above or below the web and is directed towards a pre-determined area of the web,
    an illumination system that is arranged above or below the web in order to illuminate from a pre-determined direction the area with obliquely incident light, and
    an image analysis system that is arranged to be in communication with the imaging system,
    wherein
    the imaging system is arranged to take under said illumination and during a pre-determined period several digital images of the web when the web passes in front of the imaging system, which images form a series of surface sections along a band in the web, and
    the image analysis system is arranged to calculate the variance in the pixel values in each pixel row in each image in the image sequence, and to calculate the mean value of the variances of all pixel rows of all images in the image sequence.

* * * * *